United States Patent
Choi et al.

(10) Patent No.: US 10,085,669 B2
(45) Date of Patent: Oct. 2, 2018

(54) SENSOR SYSTEM AND METHOD OF OPERATING THE SAME

(71) Applicant: Samsung Electronics Co., Ltd., Suwon-si (KR)

(72) Inventors: Chang Mok Choi, Seoul (KR); Sang Joon Kim, Hwaseong-si (KR); Min Young Mun, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 279 days.

(21) Appl. No.: 14/059,622

(22) Filed: Oct. 22, 2013

(65) Prior Publication Data

US 2014/0257129 A1   Sep. 11, 2014

(30) Foreign Application Priority Data

Mar. 5, 2013   (KR) .......................... 10-2013-0023368

(51) Int. Cl.
*A61B 5/0492* (2006.01)
*A61B 5/00* (2006.01)

(52) U.S. Cl.
CPC ............ *A61B 5/0492* (2013.01); *A61B 5/681* (2013.01); *A61B 5/7225* (2013.01)

(58) Field of Classification Search
CPC . A61B 5/04012; A61B 5/0488; A61B 5/0492; A61B 5/681; A61B 5/04004; A61B 5/6822; A61B 5/6824; A61B 5/6829
See application file for complete search history.

(56) References Cited

U.S. PATENT DOCUMENTS

| | | | | |
|---|---|---|---|---|
| 4,975,616 A | * | 12/1990 | Park | H01L 41/1132 310/339 |
| 5,331,966 A | * | 7/1994 | Bennett | A61N 1/36185 128/903 |
| 6,230,059 B1 | | 5/2001 | Duffin | |
| 6,463,322 B1 | * | 10/2002 | Lutz | A61B 5/04004 600/544 |
| 6,496,715 B1 | * | 12/2002 | Lee | A61N 1/375 600/424 |
| 6,728,564 B2 | * | 4/2004 | Lahteenmaki | A61B 5/04004 128/902 |
| 6,965,794 B2 | * | 11/2005 | Brody | A61B 5/0492 600/393 |

(Continued)

FOREIGN PATENT DOCUMENTS

JP   2007-159722 A   6/2007
JP   2011-206398 A   10/2011

(Continued)

OTHER PUBLICATIONS

Prutchi, D., "A high-resolution large array (HRLA) surface EMG system", Medical Engineering & Physics, vol. 17, No. 6, 1995, p. 442-454.*

*Primary Examiner* — Sean Dougherty
(74) *Attorney, Agent, or Firm* — NSIP Law

(57) ABSTRACT

Provided is a device for measuring a signal and a method of operating the same. The device may include electrodes attached to the device, and a control unit for determining the optimal pair of electrodes to be used for measuring the signal. Also, the device may include an output unit for measuring signals that are sensed by the electrodes.

11 Claims, 5 Drawing Sheets

(56) References Cited

U.S. PATENT DOCUMENTS

| | | | |
|---|---|---|---|
| 8,323,190 B2* | 12/2012 | Vitiello | A61B 5/0002 600/300 |
| 9,789,302 B2* | 10/2017 | Molnar | A61N 1/025 |
| 9,814,885 B2* | 11/2017 | Molnar | A61N 1/36185 |
| 9,814,886 B2* | 11/2017 | Zhou | A61N 1/3627 |
| 2002/0077534 A1* | 6/2002 | DuRousseau | G06F 3/015 600/300 |
| 2002/0193670 A1* | 12/2002 | Garfield | A61B 5/0444 600/304 |
| 2004/0054273 A1* | 3/2004 | Finneran | A61B 5/04004 600/393 |
| 2004/0243342 A1* | 12/2004 | Rekimoto | G06F 3/011 702/150 |
| 2005/0010121 A1* | 1/2005 | Ross | A61B 5/0428 600/509 |
| 2005/0073797 A1* | 4/2005 | Smith | F41H 13/0025 361/232 |
| 2005/0107654 A1* | 5/2005 | Riehl | A61N 2/006 600/9 |
| 2005/0113703 A1* | 5/2005 | Farringdon | A61B 5/0428 600/509 |
| 2006/0195159 A1* | 8/2006 | Bradley | A61N 1/36132 607/48 |
| 2007/0106343 A1* | 5/2007 | Monogue | A61B 5/0492 607/48 |
| 2007/0208269 A1* | 9/2007 | Mumford | A61B 5/0002 600/546 |
| 2008/0269581 A1* | 10/2008 | Wood | A61B 5/0031 600/345 |
| 2009/0033333 A1* | 2/2009 | Gribova | A61B 5/04 324/439 |
| 2009/0326406 A1* | 12/2009 | Tan | G06F 3/015 600/546 |
| 2010/0004715 A1* | 1/2010 | Fahey | A61H 39/002 607/48 |
| 2010/0125304 A1 | 5/2010 | Faltys | |
| 2010/0198315 A1* | 8/2010 | Martens | A61N 1/36082 607/72 |
| 2011/0015503 A1* | 1/2011 | Joffe | A61B 5/04004 600/301 |
| 2011/0208261 A1* | 8/2011 | Levine | A61N 1/36507 607/27 |
| 2011/0224665 A1* | 9/2011 | Crosby | A61B 18/1492 606/33 |
| 2011/0264002 A1* | 10/2011 | Kolen | A61B 5/1104 600/554 |
| 2012/0022347 A1* | 1/2012 | Liu | A61B 5/0488 600/316 |
| 2012/0029399 A1 | 2/2012 | Sankai | |
| 2012/0123232 A1* | 5/2012 | Najarian | A61B 5/0022 600/345 |
| 2012/0143020 A1* | 6/2012 | Bordoley | A61B 5/1114 600/301 |
| 2012/0188158 A1* | 7/2012 | Tan | A61B 5/0488 345/156 |
| 2012/0226330 A1* | 9/2012 | Kolen | A61B 5/0488 607/48 |
| 2012/0245436 A1* | 9/2012 | Rutkove | A61B 5/4519 600/301 |
| 2012/0245439 A1* | 9/2012 | Andre | A61B 5/0205 600/310 |
| 2013/0030277 A1* | 1/2013 | Fahey | A61B 5/0492 600/384 |
| 2013/0341752 A1* | 12/2013 | Kostamo | H01L 31/02005 257/490 |
| 2014/0039340 A1* | 2/2014 | Young | A61B 5/0488 600/546 |
| 2014/0152621 A1* | 6/2014 | Okayama | G06F 3/0416 345/174 |

FOREIGN PATENT DOCUMENTS

| | | |
|---|---|---|
| KR | 10-0504217 B1 | 7/2005 |
| KR | 10-0868071 B1 | 11/2008 |

* cited by examiner

SENSOR SYSTEM AND METHOD OF OPERATING THE SAME

CROSS-REFERENCE TO RELATED APPLICATIONS

This application claims the benefit under 35 U.S.C. § 119(a) of Korean Patent Application No. 10-2013-0023368, filed on Mar. 5, 2013, in the Korean Intellectual Property Office, the entire disclosure of which is incorporated herein by reference for all purposes.

BACKGROUND

1. Field

The following description relates to an sensor system and a method of operating the same.

2. Description of Related Art

An electromyography (EMG) signal, which is a signal measuring electrical activity produced by skeletal muscle, may be used for rehabilitation applications or to assist a user interface. An EMG sensor for sensing the signal may monitor muscle relaxations and contractions. Signal quality may be high or low based on the location of the EMG sensor while attached to the skin surface.

Similarly, other biological signals are affected by the location of sensors while attached to a skin surface, and signal quality generally is related to sensor position and location. Examples of other biological signals include electrocardiography (EKG) signals, electroencephalography (EEG) signals, among others.

Accordingly, the location of the EMG sensor on the skin surface is important. However, it is difficult for a person lacking anatomical knowledge to attach an EMG sensor to an intended location above a particular muscle for which electrical activity is to be sensed.

SUMMARY

In a first general aspect, there is provided a device for measuring a biological signal, the device including electrodes configured to collect measurements from a subject; and a control unit configured to select electrode combinations, each of the electrode combinations comprising at least two electrodes, and to determine an optimal electrode combination by comparing signal sizes measured for the selected electrode combinations.

The biological signal may be an electromyography (EMG) signal; the electrodes may be configured to be in contact with the subject; and the optimal electrode combination may be used to sense the EMG signal from the subject.

The electrodes may include an electrode and other electrodes; and the control unit may select the electrode combinations by grouping the electrode with each of the other electrodes in a sequential manner.

The control unit may determine that a combination of the electrode and one of the other electrodes is the optimal electrode combination in response to that combination measuring a largest signal size.

The control unit may control a single differential amplifier to measure a signal size by connecting the single differential amplifier with the at least two electrodes of the electrode combination.

The device may further include a guide unit configured to provide a command to move the subject from which measurements are to be taken according to a pattern, wherein the control unit may compare a signal size of the electrode combinations without the movement having an effect on the comparing.

The pattern may correspond to one or a combination of a muscle contraction and a muscle relaxation.

The guide unit may provide the pattern in a form of graphical information or audio information.

The bracelet member may be configured to be worn by a subject from whom measurements are to be taken, and to support the electrodes with sensing surfaces of the electrodes being in contact with the subject; and a switch may be provided on the bracelet member to connect and switch between the electrodes, wherein the control unit may select the electrode combinations using the switch.

In another general aspect, there is provided a method of operating a sensing device for measuring a biological signal, the method including providing electrodes configured to collect measurements from a subject; selecting electrode combinations, each of the electrode combinations comprising at least two electrodes; and determining an optimal electrode combination by comparing signal sizes measured for the selected electrode combinations.

The biological signal may be an electromyography (EMG) signal; the providing of the electrodes may include providing electrodes that are configured to be in contact with the subject; and the determining of the optimal electrode combination may include determining the optimal electrode combination to be used to sense the EMG signal from the subject.

The electrodes may include an electrode and other electrodes; and the selecting of the electrode combinations may include selecting the electrode combinations by grouping the electrode with each of the other electrodes in a sequential manner.

The determining of the optimal electrode combination may include determining that a combination of the electrode and one of the other electrodes is the optimal electrode combination in response to that combination measuring a largest signal size.

The method may further include controlling a single differential amplifier to measure a signal size by connecting the single differential amplifier with the at least two electrodes of the electrode combination.

The method may further include providing a command to move the subject from which measurements are to be taken according to a pattern; and comparing a signal size of the electrode combinations without the movement having an effect on the comparing.

The providing of the command may include providing a command to move the subject according to a pattern corresponding to one or a combination of a muscle contraction and a muscle relaxation.

The providing of the command may include providing the pattern in a form of graphical information or audio information.

In another general aspect, there is provided a device for measuring a signal, the device including: sensors configured to collect measurements from a subject; and an output unit configured to measure signals sensed by the sensors, wherein pairs of the sensors are sequentially connected to the output unit for determining a pair of sensors having an optimal signal.

The sensors may be arranged on a bracelet according to a shape.

The optimal signal may be determined by comparing signal sizes of signals sensed by each pair of the pairs of the sensors.

DETAILED DESCRIPTION

Figure 1:
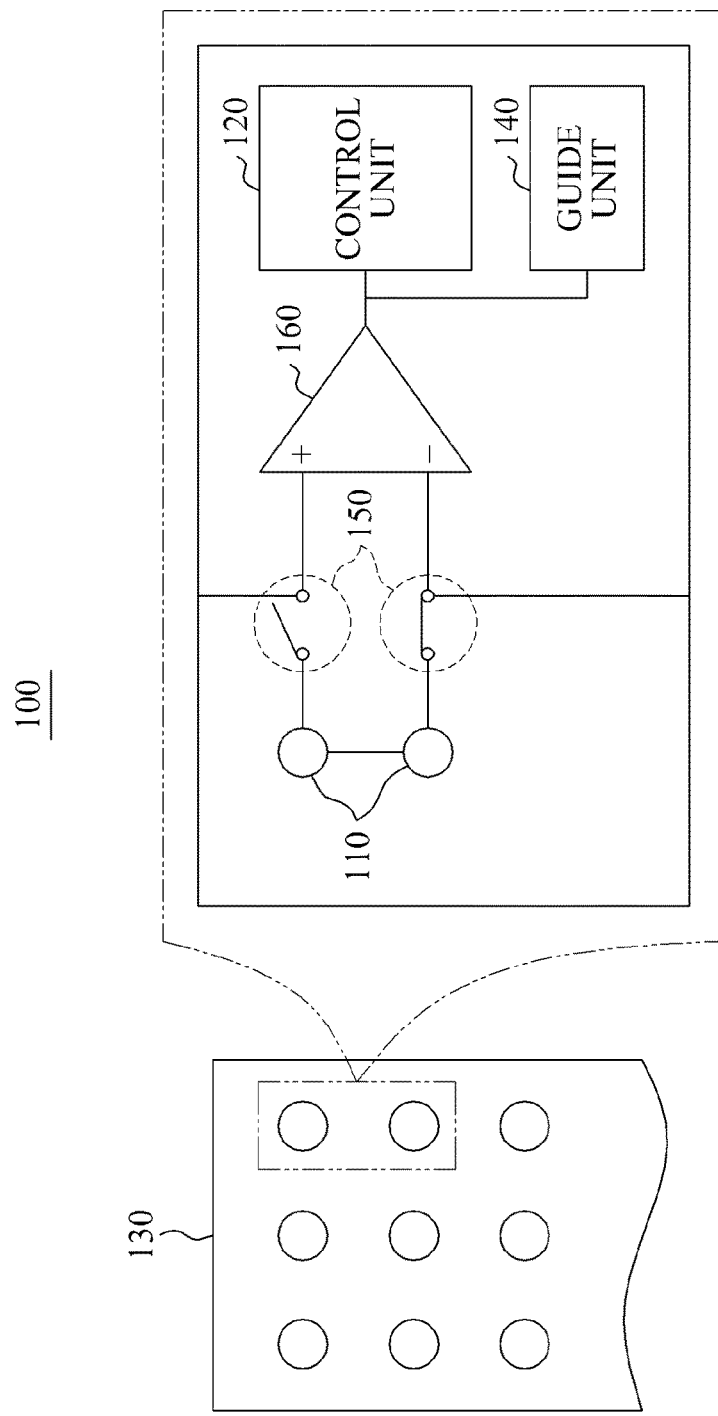
FIG. 1 is a diagram illustrating an example of an electromyography (EMG) sensor system.

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. Also, descriptions of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

The term "electrode" as used herein may represent an element or component to sense a signal generated from a subject from which measurements are to be taken while in contact with the corresponding subject. The sensed signal may be input to a differential amplifier with another signal sensed by another electrode, and may be used to measure an electromyography (EMG) signal for the corresponding subject.

For example, when a measurement is to be taken for a muscle, a plurality of electrodes may be attached to different locations on the human skin above the muscle in order to sense the signals generated from the muscle. The sensed signals may be input in pairs to a differential amplifier and may be used to measure an EMG signal for the muscle.

The plurality of electrodes in an array may be supported in a bracelet member worn by the corresponding subject. In this example, the sensing surfaces of the electrodes of the bracelet member may be in contact with the subject. Each of the electrodes of the bracelet member may sense signals generated from the muscle concurrently at each of their respective locations.

In an example, an EMG sensor system may input at least two signals among the sensed signals to a differential amplifier in a sequential manner by a switching action. The sensor system may measure a size of each signal and determine an optimal electrode combination allowing a largest signal size. This allows subsequent EMG signals to be measured accurately through the determined optimal electrode combination.

FIG. 1 is a diagram illustrating an example of an EMG sensor system 100.

Referring to FIG. 1, the EMG sensor system 100 includes electrodes 110 and a control unit 120. In an example, the EMG sensor system 100 may include a bracelet member 130, a guide unit 140, and a switch 150.

In this example, the electrodes 110 collect signals from a subject from which measurements are to be taken while in contact with the subject. In this example, the portion of the subject from which measurements are taken corresponds to a muscle of an organism. This allows the electrodes 110 to measure an EMG signal. Alternatively, signals such as electrocardiograms (EKG) for heart activity, electroencephalograms (EEG) for brain activity, and other physiological signals may be measured using the electrodes 110.

The electrodes 110 may be spaced apart according to a predetermined array, and may be attached to and contacting skin above the subject's muscle. This allows the electrodes 110 to sense various signals generated from the muscle. The signals may correspond to a signal generated in association with the muscle, for example, a bio-electric/magnetic/optic signal, a bio-impedance signal, a bio-mechanical signal, and the like.

In this example, to collect signals having a high signal to noise ratio (SNR), the electrodes 110 are disposed at an exact location corresponding to a trunk or a bulging central part of the muscle from which measurements are to be taken. However, a number of muscles, a location, a structure of muscle differentiation, and a function may be different for each individual, and finding optimal locations of the electrodes 110 while satisfying these differences may be very difficult.

For example, wrist muscles which are responsible for the movement of fingers and the wrist include about thirteen muscles on the forearm side. Further, these muscles may be arranged in overlapping layers. Accordingly, it may be impossible for a person lacking anatomical knowledge to locate and attach the electrodes 110 to a most favorable location for measurement.

Therefore, in an example, the EMG sensor system may further include the bracelet member 130 to support the plurality of electrodes 110 in a spacing pattern which corresponds to a predetermined array.

In this example, the bracelet member 130 is worn by the subject and supports the electrodes 110. The sensing surfaces of the electrodes 110 are in contact with the subject from which measurements are to be taken. The sensing surfaces sense signals generated from the subject, for which direct measurements are to be taken, while in contact with the subject. The bracelet member 130 supports the electrodes 110 for allowing the electrodes 110 to sense various signals of the subject. For example, the signals that may be measured include bio-electric/magnetic/optic signals, bio-impedance signals, bio-mechanical signals, and the like.

For example, when the bracelet member 130 is worn on the subject's wrist, the bracelet member 130 may wrap around the skin above the wrist muscles so that an area of the bracelet member 130 supporting the plurality of electrodes 110 may cover at least the wrist muscles. Accordingly, the bracelet member 130 enables collection of the signals through the plurality of electrodes 110 which are placed over all the muscles in the wrist from which measurements are to be taken.

The EMG sensor system 100 may determine the optimal electrode combination to be an electrode pair allowing the largest signal size among the plurality of electrodes 110 supported in the bracelet member 130. The EMG sensor system 100 may enable measurement of subsequent EMG signals for the corresponding subject through the determined optimal electrode combination in order to achieve high reliability EMG signal measurements.

In this example, the EMG sensor system 100 includes a control unit 120. The control unit 120 selects an electrode combination n number of times, each electrode combination including at least two electrodes among the plurality of electrodes 110. Here, 'n' denotes a natural number greater than or equal to two, and the control unit 120 may select the electrode combination n number of times.

For example, the control unit 120 selects the electrode combinations by grouping a first electrode and a second electrode among the plurality of electrodes 110 in a sequential manner.

For example, if the electrodes 110 include nine electrodes in a 3×3 array, the control unit 120 determines an arbitrary electrode among the nine electrodes to be a first electrode and one of the remaining eight electrodes to be a second electrode. Thus, the control unit 120 selects eight electrode combinations by grouping the first electrode and the second electrode in a sequential manner. Subsequently, the control unit 120 re-determines an arbitrary electrode among the remaining eight electrodes, aside from the previously selected first electrode, to be a first electrode. Thus, the control unit 120 selects seven electrode combinations by grouping the newly determined first electrode and the remaining second electrodes in a sequential manner. This electrode pairing may be performed iteratively. Accordingly, in this example, the control unit 120 selects a total number of combinations equal to $(9-1)!=36$ for nine electrodes in a 3×3 array.

In this example, the control unit 120 determines an optimal electrode combination to be used for sensing the EMG signal by comparing signal sizes measured for each of the electrode combinations. In an example, the signal sizes are measured through an operation by a differential amplifier 160.

For example, the control unit 120 determines the optimal electrode combination to be a combination of the first electrode and the second electrode when a largest signal size is measured. In this example, the control unit 120 controls the single differential amplifier 160 to measure the signal sizes by contacting the single differential amplifier 160 with the at least two electrodes included in the electrode combination.

During the measurement of the signal sizes by the differential amplifier 160, the EMG sensor system 100 may induce the subject to make a movement for obtaining optimum measurement. Accordingly, the EMG sensor system 100 may further include a guide unit 140 to provide a command to move the corresponding subject in a predetermined pattern.

In this example, the guide unit 140 provides a command to move the muscle or muscles for which measurements are taken in a pattern corresponding to contraction and/or relaxation.

For example, when the muscles for which measurements are taken are wrist muscles, the guide unit 140 may provide a command associated with a wrist raising pattern to contract the wrist muscles to a maximum extent. This allows measurement of the signal sizes for each of the electrode combinations under the highest tension. Also, in another example, the guide unit 140 may provide a command associated with a wrist laying-down pattern to reduce the tension of the wrist muscles. This allows measurement of the signal sizes for each of the electrode combinations under relaxation.

In this example, the command provided by the guide unit 140 for subject movement according to a predetermined pattern may ensure equal conditions for measuring the signal sizes using each of the electrode combinations. This ensures reliability in the subsequent comparison of the signal sizes.

The guide unit 140 may provide the pattern in a form of graphical information or audio information. Accordingly, the guide unit 140 may be connected to a display to provide the pattern in a form of graphical information by displaying the pattern. For example, the guide unit 140 may induce the maximum contraction of the wrist muscles from which measurements are to be taken by displaying graphical information associated with a wrist raising movement through the external display.

In another example, the guide unit 140 may be connected to a speaker to provide the pattern in the form of audio information by voicing the pattern to be performed. For example, the guide unit 140 may induce the maximum relaxation of the wrist muscles from which measurements are to be taken by outputting audio information associated with a wrist laying-down movement through the external speaker.

In this example, the EMG sensor system 100 allows measurement of the signal sizes for each of the electrode combinations under the same condition. For example, the EMG sensor system 100 allows measurement in a condition having maximum signal size output from the corresponding electrode combinations.

In the selection of electrode combinations, the EMG sensor system 100 may select a particular electrode pair to be an electrode combination by switching between the plurality of electrodes 110. Accordingly, the EMG sensor system 100 may further include a switch 150.

In this example, the switch 150 selects a first electrode to be connected with an input terminal of the differential amplifier 160 and a second electrode to be connected with an opposite input terminal of the differential amplifier 160 by a sequential switching action.

Hereinafter, a further detailed description of selecting the electrode combination by the switch 150 is provided with reference to FIG. 2.

Figure 2:
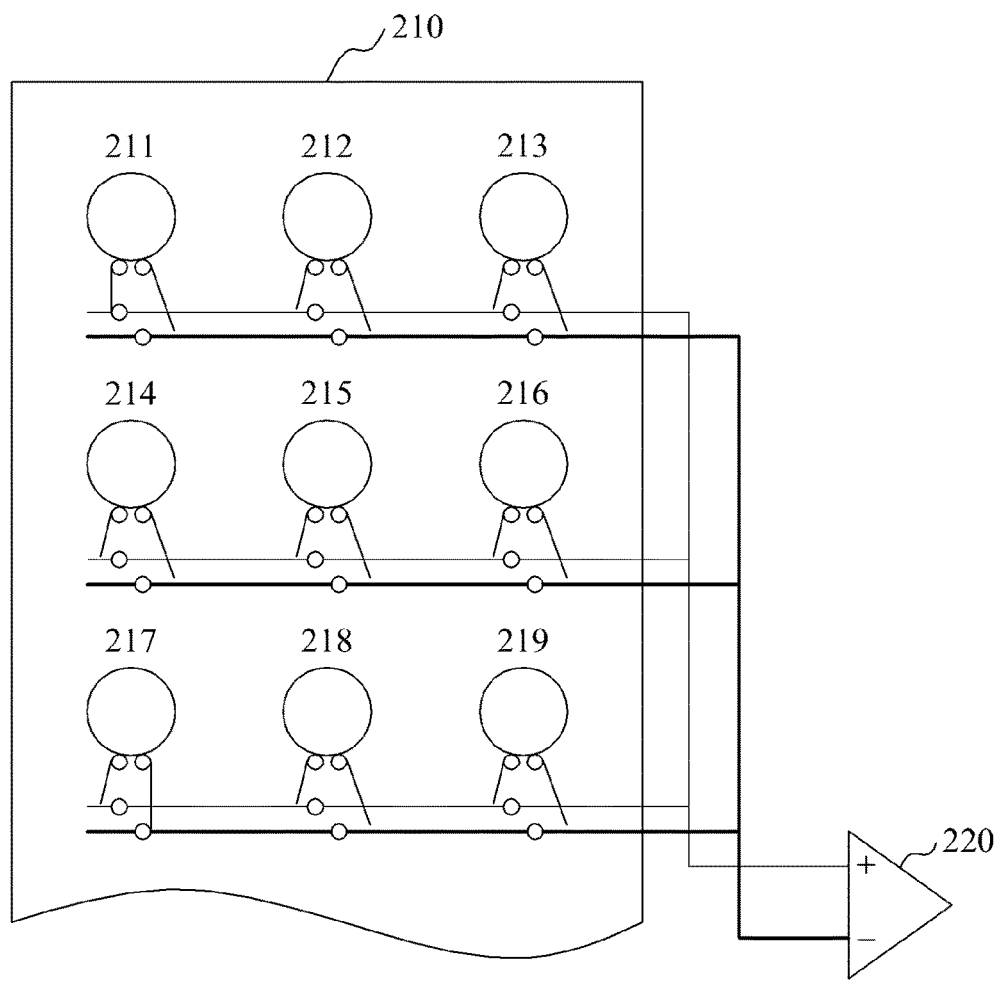
FIG. 2 is a diagram illustrating an example of sequential electrode combination selection by a switch.

FIG. 2 is a diagram illustrating an example of sequential electrode combination selection by a switch.

Referring to FIG. 2, a bracelet member 210 may support a plurality of electrodes 211-219 having a predetermined array spacing. The plurality of electrodes 211-219 may have a diameter in a range of several millimeters (mm) to several centimeters (cm). The electrode diameter may be determined based on a magnitude of the SNR and a width of the bracelet member 210.

Each of the electrodes 211-219 may be connected to the two input terminals of the differential amplifier 220 with a switch. The switch may select an electrode pair among the electrodes 211-219 in a sequential manner by switching between the electrodes 211-219 and establishing a connection to the input terminals of the differential amplifier 220.

In this example, the switch selects electrode combinations by switching ON and OFF the electrodes 211-219 and the differential amplifier 220 in an alternating manner. Also, the control unit 120 may determines the optimal electrode combination an electrode combination which allows the largest signal size while the subject maintains a gesture or position.

For example, in FIG. 2, an arbitrary electrode 211 is determined as the first electrode and a signal sensed by the electrode 211 may be input to an input terminal of the differential amplifier 220 by closing the switch between the electrode 211 and the differential amplifier 220. Also, signals sensed by the second electrodes 212-219 may be input to an opposite input terminal of the differential amplifier 220 by closing the switches between the second electrodes 212-219 and the differential amplifier 220. In this example, the switches for the second electrode 212-219 may be closed in a sequential manner under the control of the control unit 120 of FIG. 1.

Subsequently, the control unit 120 may arbitrarily determine a different electrode 212 among the remaining eight electrodes 212-219 as the first electrode, and select seven electrode combinations by grouping the electrode 212 with the remaining seven electrodes 213-219 in a sequential manner. This electrode combination selection may be performed iteratively until all possible electrode combinations resulting from combining the nine electrodes 211-219 are selected.

The differential amplifier 220 may measure a signal size for a corresponding electrode combination each time a signal is input through the two opposite input terminals. Accordingly, in this example, the control unit 120 forms a plurality of electrode combinations by a switching action, each electrode combination including a first electrode and a second electrode, and the differential amplifier 220 measures a signal size for each of the plurality of electrode combinations. Subsequently, the control unit 120 determines an electrode combination as the optimal combination allowing the largest signal size among the measured signal sizes. This allows the electrode pair having the highest quality EMG signal to be set automatically for optimum recognition of subsequent user gestures.

In an example, the EMG sensor system determines the optimal electrode pair allowing the highest quality EMG signal using a bracelet. Thus, despite a user's lack of anatomical knowledge about individual muscles, the position of the electrodes may be optimized. Also, in this example, the EMG sensor system enables efficient use of a gesture user interface (UI) through the determined electrode pair.

Further, in this example, the EMG sensor system has a power consumption reduction effect in a mobile environment by using a fewer number of differential amplifiers than the number of electrodes or by using a single differential amplifier.

Figure 3:
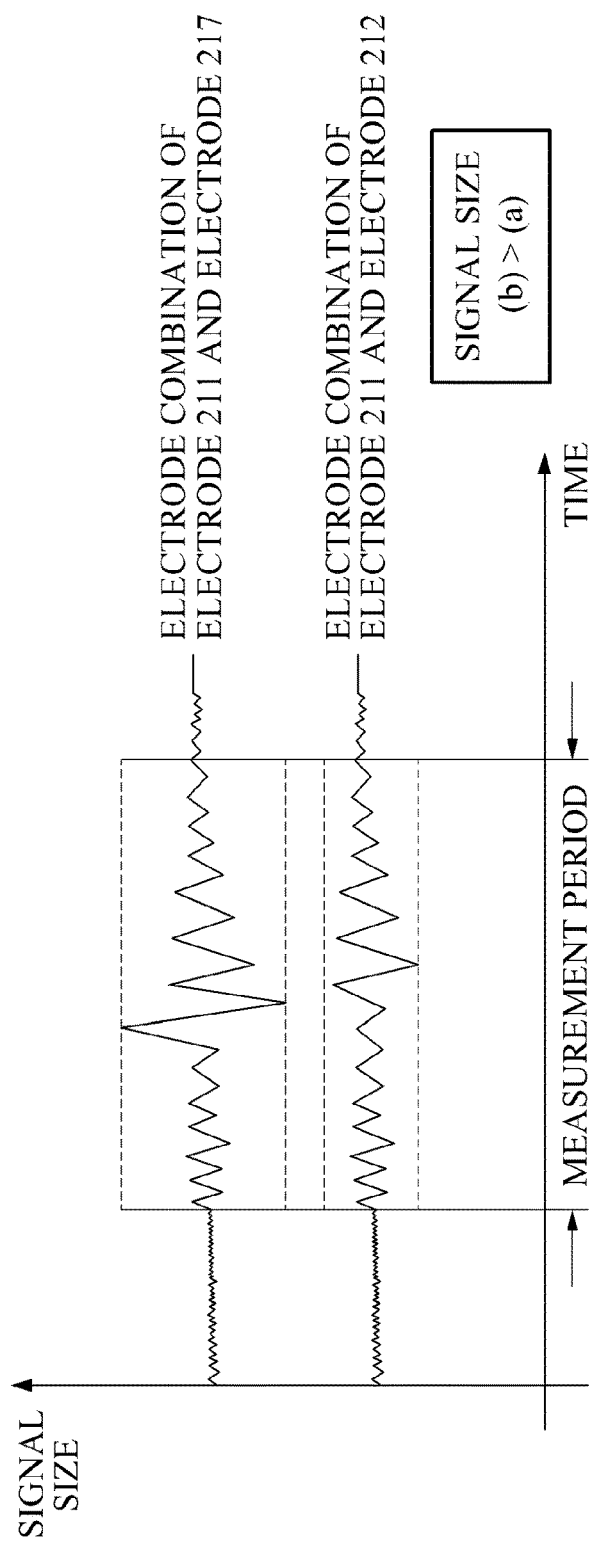
FIG. 3 is a graph illustrating an example of a comparison of signal sizes for optimal electrode combination determination.

FIG. 3 is a diagram illustrating an example of optimal electrode combination determination through signal size comparison.

Referring to FIGS. 2 and 3, the EMG sensor system selects a plurality of electrode combinations, each electrode combination including at least two electrodes of the bracelet member 210, and compares signal sizes of the electrode combinations.

For example, the EMG sensor system selects electrode 211 as a first electrode and each of the remaining electrodes 212-219 as a second electrode. Electrode combinations are formed by grouping the electrode 211 with each of the second electrodes 212-219 in a sequential manner.

Subsequently, the EMG sensor system measures the signal size for each of the electrode combinations and compares the measured signal sizes.

In FIG. 3, an example of comparing signal sizes for two electrode combinations among the plurality of selected electrode combinations is illustrated.

In (a) of FIG. 3, a signal size measured for a combination of the electrode 211 and the electrode 212 of FIG. 2 is illustrated. In this example, the differential amplifier 220 of FIG. 2 receives an input of the signal sensed by the electrode 211 and an input of the signal sensed by the electrode 212 through the two input terminals. The differential amplifier 220 measures a signal size for a combination of the electrode 211 and the electrode 212.

Also, the differential amplifier 220 may receive an input of the signal sensed by the electrode 211 and the signal sensed by the electrode 217 through the input terminals. The differential amplifier 220 measures a signal size for a combination of the electrode 211 and the electrode 217 as shown in (b) of FIG. 3.

Subsequently, the EMG sensor system may compare the signal size shown in (a) of FIG. 3 to the signal size shown in (b) of FIG. 3, and determine the combination of the electrode 211 and the electrode 217 to be an electrode combination allowing a larger signal size during the same measurement period.

Accordingly, in this example, the EMG sensor system recognizes that the signal size measured for the combination of the electrode 211 and the electrode 217 is largest, and determines that the combination of the electrode 211 and the electrode 217 is the optimal electrode combination.

Figure 4:
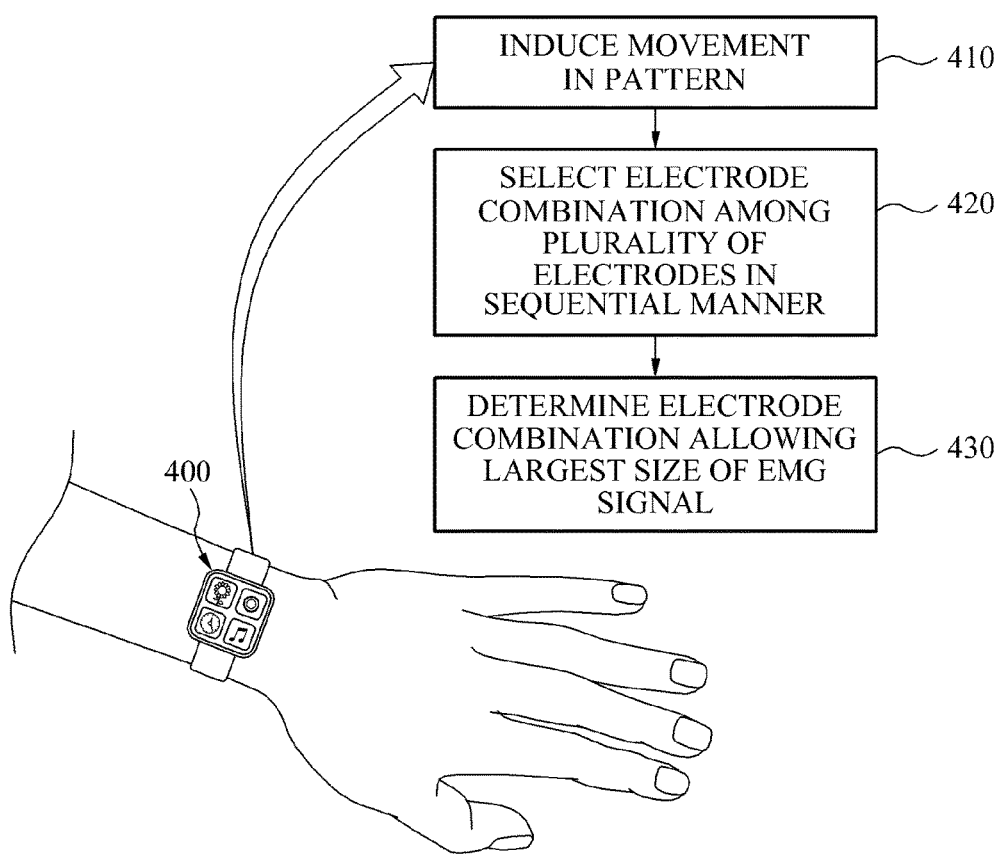
FIG. 4 is a diagram illustrating an example of optimal electrode combination determination for a subject moving in a predetermined pattern.

FIG. 4 is a diagram illustrating an example of optimal electrode combination determination for a subject moving in a predetermined pattern.

Referring to FIG. 4, in 410, the guide unit 140 of FIG. 1 induces a subject to move a body part, from which measurements are to be taken using the bracelet member 400, in a predetermined pattern. In this example, the bracelet member 400 wraps around the wrist for measuring signals affiliated with wrist muscles. The guide unit 140 may provide audio information through a speaker instructing a user to raise the wrist or move the wrist according to a particular pattern.

In this example, as the wrist is raised, muscles of the wrist are contracted and each of the electrodes supported in the bracelet member 400 obtain a signal generated from the wrist muscles.

In 420, the control unit 120 selects electrode combinations among the plurality of electrodes in a sequential manner. The control unit 120 selects the electrode combinations by pairing the electrodes iteratively through switching between the electrodes in such a state that sensing surfaces of the electrodes are in contact with the wrist. For each of the selected electrode combinations, each electrode included in the electrode combination may be connected to each input terminal of the differential amplifier 160 of FIG. 1. Subsequently, the differential amplifier 160 may measure a signal size of an EMG signal for a corresponding electrode combination.

In 430, after the signal size is measured for each of the selected electrode combinations, the control unit 120 determines the electrode combination which allows the largest signal size of the EMG signal to be the optimal electrode combination. For example, the control unit 120 may determine and verify which electrode combination allows the largest signal size by comparing the EMG signal sizes measured during the same sensing period.

In this example, the electrode pair determined to be the optimal electrode combination are regarded as electrodes disposed at the optimum location to sense the signal generated from the muscle which measurements are taken. For example, this optimal location may be a trunk of the muscle. This optimal location may be used for measuring subsequent EMG signals.

However, the electrode pair determined to be the optimal electrode combination may be valid only for the subject wearing the bracelet member 400 and from which measurements are to be taken. When the bracelet member 400 is moved and worn by another subject, the EMG sensor system may determine a different pair of electrodes as the optimal electrode combination.

In an example, the EMG sensor system determines the optimal electrode pair for measurement of an EMG signal in a simple manner by providing a switch-type connection structure to connect a plurality of electrodes attached to an inner surface of a bracelet with a fewer number of differential amplifiers than the number of electrodes.

Further, in an example, the EMG sensor system enables a user to make a gesture of a predetermined pattern using the bracelet member, and provides a method of automatically determining an electrode-differential amplifier pathway allowing the largest signal size of the EMG signal.

Hereinafter, a further detailed description of operation of the EMG sensor system 100 is provided.

Figure 5:
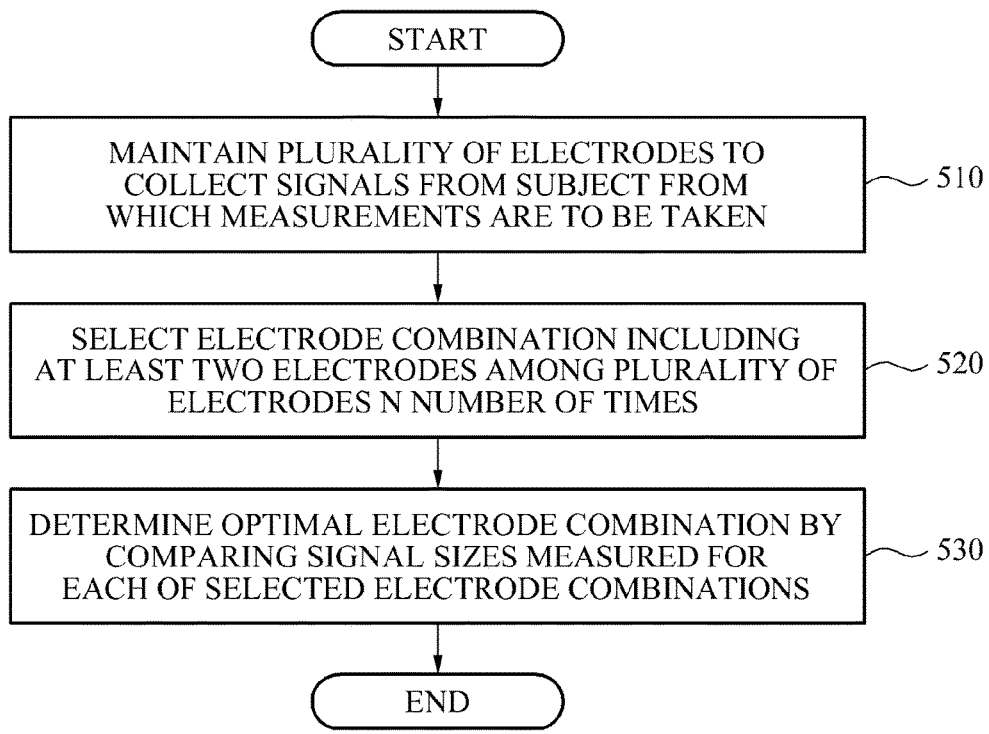
FIG. 5 is a flowchart illustrating an example of a method of operating the EMG sensor system.

FIG. 5 is a flowchart illustrating an example of a method of operating the EMG sensor system.

Referring to FIG. 5, in 510, the EMG sensor system maintains a plurality of electrodes to collect signals from a subject from which measurements are to be taken. In 510, the plurality of electrodes collect signals from the subject from which measurements are to be taken while in contact with the corresponding subject. In this example, the body part of the subject from which measurements are to be taken may correspond to, for example, a muscle of the subject requiring measurement of an EMG signal.

The plurality of electrodes may be spaced apart according to a predetermined array and may be attached to and in contact with skin above the muscle in order to sense various signals generated from the muscle. The signals may correspond to signals generated in association with the muscle, for example, bio-electric/magnetic/optic signals, bio-impedance signals, bio-mechanical signals, and the like.

In this instance, to collect signals having a high SNR, disposing the electrodes at an exact location corresponding to a trunk or a bulging central part of the muscle from which measurements are to be taken may be important. However, a number of muscles, a location, a structure of muscle differentiation, and a function may be different for each individual, and finding an optimal location of the electrodes while satisfying these differences may be rather difficult.

For example, wrist muscles responsible for the movement of the fingers and the wrist may include about thirteen muscles on the forearm side, and these muscles may be arranged in overlapping layers. Accordingly, it may be impossible for a person lacking anatomical knowledge to locate and attach the electrodes to a most favorable location for measurement.

Accordingly, a plurality of electrodes may be supported in the bracelet member according to a predetermined array spacing.

When the bracelet member is worn by the subject from which measurements are to be taken, the bracelet member may support the plurality of electrodes with sensing surfaces of the electrodes in contact with the corresponding subject. The sensing surfaces may correspond to surfaces for sensing signals generated from the subject, and for direct measurement of signals while in contact with the corresponding subject. The bracelet member may support the plurality of electrodes in order to sense various signals such as bio-electric/magnetic/optic signals, bio-impedance signals, bio-mechanical signals, and the like.

For example, when the bracelet member is worn on the wrist, the bracelet member may wrap around the skin above the wrist muscles so that an area of the bracelet member supporting the plurality of electrodes may cover at least the wrist muscles. Accordingly, the bracelet member may enable collection of the signals through the plurality of electrodes contacting all wrist muscles from which measurements are to be taken.

In 520, the EMG sensor system selects an electrode combination an n number of times, each electrode combination including at least two electrodes among the plurality of electrodes. Here, 'n' denotes a natural number greater than or equal to two, and the EMG sensor system selects electrode combinations an n number of times corresponding to a total number of iterations that may be considered from the plurality of electrodes.

In 520, the EMG sensor system selects the electrode combination by grouping a first electrode and a second electrode among the plurality of electrodes in a sequential manner.

When the plurality of electrodes include nine electrodes having a 3×3 array spacing, the EMG sensor system determines an arbitrary electrode among the nine electrodes to be a first electrode and one of the remaining eight electrodes to be a second electrode. Accordingly eight electrode combinations may be selected by grouping the first electrode and the second electrodes in a sequential manner. Subsequently, the EMG sensor system may re-determine an arbitrary electrode (i.e. determine a new electrode) among the remaining eight electrodes (not including the previously determined first electrode) to be the newly determined first electrode. Seven electrode combinations may be selected by grouping the re-determined first electrode and the remaining second electrodes other than the re-determined first electrode in a sequential manner. This electrode pairing may be performed iteratively, and for nine electrodes having a 3×3 array spacing, the control unit 120 may select a total number of electrode combinations equal to (9−1)!=36.

In 530, the EMG sensor system determines an optimal electrode combination to be used for sensing the EMG signal by comparing signal sizes measured for each of the selected electrode combinations. In this example, the signal sizes may be measured through an operation by the differential amplifier 160.

In 530, the EMG sensor system determines an electrode pair allowing the largest signal size among the plurality of electrodes supported in the bracelet member as the optimal electrode combination. This enables measurement of subsequent EMG signals for the corresponding subject through the determined optimal electrode combination to achieve high reliability EMG signal measurements.

For example, the EMG sensor system may determine a combination of the first electrode and the second electrode when a largest signal size is measured as the optimal electrode combination. In this example, the EMG sensor system controls a single differential amplifier to measure the signal sizes by contacting the single differential amplifier with the at least two electrodes included in the electrode combination.

In the measurement of the signal sizes by the differential amplifier, the EMG sensor system may induce the corresponding subject to make a movement for optimum measurement. Accordingly, the EMG sensor system provides a command to move a body part to be measured according to a predetermined pattern.

In an example, the EMG sensor system provides a command to move muscles in a pattern corresponding to contraction and/or relaxation.

For example, when the muscles from which measurements are to be taken correspond to wrist muscles, the EMG sensor system may provide a command associated with a wrist raising pattern to contract the wrist muscles to a maximum extent. This allows measurement of signal sizes for each of the electrode combinations under the highest tension. Also, according to another example, the EMG sensor system may provide a command associated with a wrist laying-down pattern to reduce the tension of the wrist muscles. This allows measurement of the signal size for each of the electrode combinations under relaxation.

The command provided requesting movement of the body part in accordance with a predetermined pattern may ensure equal conditions for measuring the signal sizes of each of the electrode combinations. This ensures reliability in the subsequent comparison of the signal sizes.

Also, the EMG sensor system may provide the pattern in a form of graphical information or audio information. Accordingly, the EMG sensor system may be connected to a display to provide the pattern in a form of graphical information by displaying the pattern. For example, the EMG sensor system may induce the maximum contraction of the wrist muscles from which measurements are to be taken by displaying graphical information associated with the wrist raising pattern through an external display.

Also, in another example, the EMG sensor system may be connected to a speaker to provide the pattern in the form of audio information by voicing the pattern to be performed. For example, the EMG sensor system may induce the maximum relaxation of the wrist muscles from which measurements are to be taken by outputting audio information associated with the wrist laying-down pattern through an external speaker.

Accordingly, the EMG sensor system allows measurement of the signal sizes for each of the electrode combinations under the same condition, such as a condition where a maximum level of a signal size is output for each corresponding electrode combination.

In this example, the EMG sensor system selects a particular electrode pair to be an electrode combination by switching between the plurality of electrodes. Accordingly, the EMG sensor system further includes a switch.

For example, the switch selects a first electrode to be connected with an input terminal of the differential amplifier and a second electrode to be connected with an opposite input terminal of the differential amplifier by a sequential switching action.

In this example, the EMG sensor system determines an optimal electrode pair by providing a switch-type connection structure to connect a plurality of electrodes attached to an inner surface of a bracelet with a fewer number of differential amplifiers than the number of the electrodes.

While the Specification describes electrodes for use with a biological signal such as an EEG, it should be appreciated that the description provided also includes determining the best position or location for sensors in general. In addition, it is noted that the differential amplifier may be an output unit which receives the sensed signal from the sensors or electrodes to determine the best position of the sensors.

Also, the EMG sensor system may enable a user to make a gesture of a predetermined pattern while wearing the bracelet member, and provide a method of automatically determining the electrode-differential amplifier pathway allowing the largest signal size of the EMG signal.

The EMG sensor system 100, electrodes 110, control unit 120, bracelet member 130, guide unit 140, switch 150, and differential amplifier 160 described above may be implemented using one or more hardware components, or a combination of one or more hardware components and one or more software components. A hardware component may be, for example, a physical device that physically performs one or more operations, but is not limited thereto. Examples of hardware components include controllers, microphones, amplifiers, low-pass filters, high-pass filters, band-pass filters, analog-to-digital converters, digital-to-analog converters, and processing devices.

A processing device may be implemented using one or more general-purpose or special-purpose computers, such as, for example, a processor, a controller and an arithmetic logic unit, a digital signal processor, a microcomputer, a field-programmable array, a programmable logic unit, a microprocessor, or any other device capable of running software or executing instructions. The processing device may run an operating system (OS), and may run one or more software applications that operate under the OS. The processing device may access, store, manipulate, process, and create data when running the software or executing the instructions. For simplicity, the singular term "processing device" may be used in the description, but one of ordinary skill in the art will appreciate that a processing device may include multiple processing elements and multiple types of processing elements. For example, a processing device may include one or more processors, or one or more processors and one or more controllers. In addition, different processing configurations are possible, such as parallel processors or multi-core processors.

Software or instructions for controlling a processing device, such as those described in FIGS. 3, 4, and 5, to implement a software component may include a computer program, a piece of code, an instruction, or some combination thereof, for independently or collectively instructing or configuring the processing device to perform one or more desired operations. The software or instructions may include machine code that may be directly executed by the processing device, such as machine code produced by a compiler, and/or higher-level code that may be executed by the processing device using an interpreter. The software or instructions and any associated data, data files, and data structures may be embodied permanently or temporarily in any type of machine, component, physical or virtual equipment, computer storage medium or device, or a propagated signal wave capable of providing instructions or data to or being interpreted by the processing device. The software or instructions and any associated data, data files, and data structures also may be distributed over network-coupled computer systems so that the software or instructions and any associated data, data files, and data structures are stored and executed in a distributed fashion.

For example, the software or instructions and any associated data, data files, and data structures may be recorded, stored, or fixed in one or more non-transitory computer-readable storage media. A non-transitory computer-readable storage medium may be any data storage device that is capable of storing the software or instructions and any associated data, data files, and data structures so that they can be read by a computer system or processing device. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, or any other non-transitory computer-readable storage medium known to one of ordinary skill in the art.

Functional programs, codes, and code segments for implementing the examples disclosed herein can be easily constructed by a programmer skilled in the art to which the examples pertain based on the drawings and their corresponding descriptions as provided herein.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A device for measuring a biological signal, the device comprising:
    electrodes configured to collect measurements from a subject;
    a single differential amplifier configured to measure a size of the measured biological signal; and
    a controller configured to:
       select electrode combinations, each of the electrode combinations including at least two electrodes selected from the electrodes;
       control the single differential amplifier to connect to at least two electrodes included in each of the selected electrode combinations, wherein the single differential amplifier is configured to measure respective signal sizes from the at least two electrodes; and
       determine, as an optimal electrode combination, a combination of a first electrode and a second electrode by comparing the respective signal sizes measured for each of the selected electrode combinations with each other, the optimal electrode combination having a determined largest biological signal size based on a result of the comparing.

2. The device of claim 1, wherein
    the biological signal is an electromyography (EMG) signal;
    the electrodes are configured to be in contact with the subject; and
    the optimal electrode combination is to be used to sense the EMG signal from the subject.

3. The device of claim 1, wherein
    the controller selects the electrode combinations by grouping the electrodes in a sequential manner, the electrodes including the first electrode and the second electrode.

4. The device of claim 1, further comprising:
    a guide processor configured to provide a command to move the subject from which the measurements are to be taken according to a pattern, wherein the controller compares the respective signal sizes of each of the selected electrode combinations without the movement having an effect on the comparing.

5. The device of claim 4, wherein the pattern corresponds to one or a combination of a muscle contraction and a muscle relaxation.

6. The device of claim 4, wherein the guide processor provides the pattern in a form of graphical information or audio information.

7. The device of claim 1, further comprising:
    a bracelet member configured to be worn by the subject from whom the measurements are to be taken, and to support the electrodes with sensing surfaces of the electrodes being in contact with the subject; and
    a switch provided on the bracelet member to connect and switch between the electrodes,
    wherein the controller selects the electrode combinations using the switch.

8. A device for measuring a biological signal, the device comprising:
    sensors configured to collect measurements from a subject;
    a single differential amplifier configured to measure biological signals sensed by the sensors; and
    a controller configured to determine an optimal pair of sensors, among the sensors, having a determined largest biological signal size, the determining of the optimal pair of sensors including selecting pairs of at least two sensors from the sensors, and sequentially connecting the selected at least two sensors to the single differential amplifier.

9. The device of claim 8, wherein the sensors are arranged on a bracelet according to a shape.

10. The device of claim 8, wherein the determining of the optimal pair of sensors further includes comparing sizes of the respective biological signals sensed by each of the selected pairs of the at least two sensors.

11. The device of claim 8, wherein the sensors correspond to electrodes.

* * * * *